United States Patent
Jones et al.

(10) Patent No.: US 7,073,383 B2
(45) Date of Patent: Jul. 11, 2006

(54) APPARATUS AND METHOD FOR DETERMINING CLAMPING STATUS OF SEMICONDUCTOR WAFER

(75) Inventors: William Jones, Phoenix, AZ (US); Paul Moroz, Marblehead, MA (US); Andrej Mitrovic, Phoenix, AZ (US)

(73) Assignee: Tokyo Electron Limited, Tokyo (JP)

( * ) Notice: Subject to any disclaimer, the term of this patent is extended or adjusted under 35 U.S.C. 154(b) by 112 days.

(21) Appl. No.: 10/478,689

(22) PCT Filed: May 9, 2002

(86) PCT No.: PCT/US02/14582

§ 371 (c)(1),
(2), (4) Date: Dec. 8, 2003

(87) PCT Pub. No.: WO02/101377

PCT Pub. Date: Dec. 19, 2002

(65) Prior Publication Data

US 2004/0149041 A1     Aug. 5, 2004

Related U.S. Application Data

(60) Provisional application No. 60/296,145, filed on Jun. 7, 2001.

(51) Int. Cl.
*G01N 29/40* (2006.01)

(52) U.S. Cl. ...................................................... 73/627
(58) Field of Classification Search .................. 73/627, 73/625, 629
See application file for complete search history.

(56) References Cited

U.S. PATENT DOCUMENTS

| | | | |
|---|---|---|---|
| 4,137,991 A | 2/1979 | Melcher et al. | 181/142 |
| 5,436,790 A | 7/1995 | Blake et al. | 361/234 |
| 5,440,929 A | 8/1995 | Huang et al. | 73/628 |
| 5,948,986 A | 9/1999 | Brown | 73/630 |
| 5,956,837 A | 9/1999 | Shiota et al. | 29/539 |
| 6,403,322 B1 * | 6/2002 | Fischer | 435/6 |

FOREIGN PATENT DOCUMENTS

| | | | |
|---|---|---|---|
| JP | 04062021 | | 2/1992 |
| JP | 04175120 A | * | 6/1992 |
| JP | 11097508 A | * | 4/1999 |
| TW | 264535 | | 12/1995 |
| TW | 429206 | | 4/2001 |
| WO | 9108456 | | 6/1991 |

* cited by examiner

*Primary Examiner*—Hezron Williams
*Assistant Examiner*—Rose M. Miller
(74) *Attorney, Agent, or Firm*—Oblon, Spivak, McClelland, Maier & Neustadt, P.C.

(57) ABSTRACT

An apparatus determines how well a semiconductor wafer (4) is clamped to a support member (1). The apparatus has at least one ultrasonic transducer (2a,2b,2c,2d) configured to emit ultrasonic energy (3) toward an interface between the wafer (4) and the support member (1) so that the interface generates echo signals, and a data processing unit (11) configured to analyze the echo signals to arrive at a determination as to how well the semiconductor wafer (4) is clamped to the support member (1before semiconductor process is started. A first method ensures that a wafer (4) is securely clamped to a support member before a semiconductor process is started. A second method verifies proper de-clamping of a semiconductor wafer (4) from a support member (1) before the semiconductor wafer (4) is removed from the support member (1) upon completion of a semiconductor process.

39 Claims, 6 Drawing Sheets

APPARATUS AND METHOD FOR DETERMINING CLAMPING STATUS OF SEMICONDUCTOR WAFER

BACKGROUND OF THE INVENTION

1. Field of the Invention

The present invention relates to apparatus and methods for reliably determining when a semiconductor wafer is securely clamped in place. More specifically, the invention relates to apparatus and methods that use ultrasonic techniques to reliably determine whether or not a semiconductor wafer is securely clamped in place on a support member.

2. Discussion of the Background

Plasma processing of silicon wafers to transfer a pattern of an integrated circuit from the photolithographic mask to the silicon, or to deposit dielectric or conductive films on the substrate, have become standard methods in the industry. In conventional plasma processors, the silicon wafer being processed is held in close proximity to the wafer chuck, ordinarily by electrostatic force. This system is quite effective in holding the wafer securely to the chuck during processing, permitting good heat transfer between the wafer and the other components in the processing system.

However, all modem manufacturing plasma processors use automatic robotic systems to load the wafer on and off of the wafer chuck. It is essential, therefore, that the status of the clamping between the wafer and the wafer chuck be confirmed after the wafer has been loaded onto the wafer chuck and before it is removed by the loading arm. Failure of clamping after loading the wafer onto the wafer chuck will result in poor quality and uniformity of the process, resulting in poor yields and poor quality of the finished devices.

During deposition of metal on a silicon wafer to form conductive paths that are the electrical interconnects in an integrated circuit, for example, large amounts of electrical energy are delivered to the process chamber to transfer the metal ions from the source of metal to the wafer. As the metal is deposited, energy is delivered to the wafer and if the wafer is not cooled, heat may damage the electrical devices. To keep the wafer cool and to promote formation of the desired metallurgical compounds on the surface of the wafer, the wafer is electrostatically clamped to a chilled surface and a gas is introduced behind the wafer to enhance heat transfer from the wafer to the chilled surface Because the gas behind the wafer is pressurized to enhance heat transfer, if the wafer is not securely clamped before the gas is introduced behind the wafer, the wafer will float on the cushion of gas, away from its position on the chilled surface. Thus, it is desirable to verify that the wafer is properly clamped before introducing the gas behind the wafer, and to maintain a secure clamp as long as pressurized gas is present behind the wafer.

When the processing is complete, the electrostatic potential holding the wafer to the wafer chuck is turned off. However, residual electrostatic charges may inhibit release of the wafer. In this case, when the robotic system attempts to remove the wafer from the wafer chuck, the wafer may be broken. This is catastrophic, because not only is the valuable wafer lost, it is usually necessary to do a complete tear down and clean out of the processing chamber, costing valuable time and manpower as well as lost production time on the equipment.

Therefore, it is desirable to continuously monitor the status of the clamping between the wafer and wafer chuck.

One alternative method for detecting the presence of a wafer and whether the wafer is satisfactorily clamped is by measuring the capacitance between the wafer and the surface on which the wafer is clamped. The capacitance is measured by injecting a sample RF signal onto an electrode under the wafer and measuring the intensity of the sample frequency RF on a second electrode under the wafer.

A second alternative method for detecting whether the wafer is satisfactorily clamped is by measuring the flow necessary to maintain a pressure of gas under the wafer. By using very small flows to produce a very slight pressure under the wafer, it may be possible to determine the quality of the clamp of the wafer prior to applying gas pressure under the wafer. Similarly, this technique may be used to determine whether the wafer has been de-clamped from the surface. This technique, however, is not useful for monitoring the clamp status during processing of the wafer since it relies on the opportunity to adjust the pressure or flow of gas behind the wafer. Also, variations in the surface of the wafer may result in variations in flow even though the wafer is securely clamped to the surface.

U.S. Pat. No. 5,271,274 (Khuri-Yakub et al.) discloses a method using ultrasonic acoustic waves to determine the presence and thickness of films on a substrate. The echo of the ultrasonic wave or the phase of the echo is used to measure the thickness of deposited films on a substrate such as a silicon wafer. U.S. Pat. No. 6,019,000 (Stanke et al.) utilizes ultrasonic acoustic waves to perform in-situ measurement of deposition on reactor chamber members. This system also permits the determination of the degree of erosion of chamber members. Both patents utilize reflection of the ultrasonic waves from the surfaces and interfaces between the members and films to determine the presence and thickness of the films. However, neither patent solves the problems of monitoring the status of the clamping between a wafer and a wafer chuck, and of determining when the wafer has been completely released by electrostatic forces holding it to the wafer chuck. It is to fulfill these needs, among others, that the present invention is directed.

SUMMARY OF THE INVENTION

An important feature of the invention is the use of ultrasonic transducers to determine the status of the clamping of a wafer to a wafer chuck. The status of the wafer clamping is determined in real time continually during the wafer processing cycle. Thus, mis-processing of wafers because of improper or incomplete clamping is avoided. Also, since the degree of clamping force is measured by continually monitoring the intensity of a reflected signal, this measurement is used to determine the effectiveness of the electrostatic chuck and to timely detect incipient failure of the clamp.

Another important feature is the use of ultrasonic transducers to determine when the wafer has been completely released by the electrostatic forces holding it to the wafer chuck. The complete release of the wafer by the electrostatic chuck is determined, thus permitting the safe removal of the wafers from the processing chamber by a robotic system, without danger of breaking the wafer.

Other objects, features and advantages of the present invention will be apparent to those skilled in the art upon a reading of this specification including the accompanying drawings.

BRIEF DESCRIPTION OF THE DRAWINGS

The invention is better understood by reading the following Detailed Description of the Preferred Embodiments with reference to the accompanying drawing figures, in which like reference numerals refer to like elements throughout, and in which.

DETAILED DESCRIPTION OF THE PREFERRED EMBODIMENTS

Figure 1:
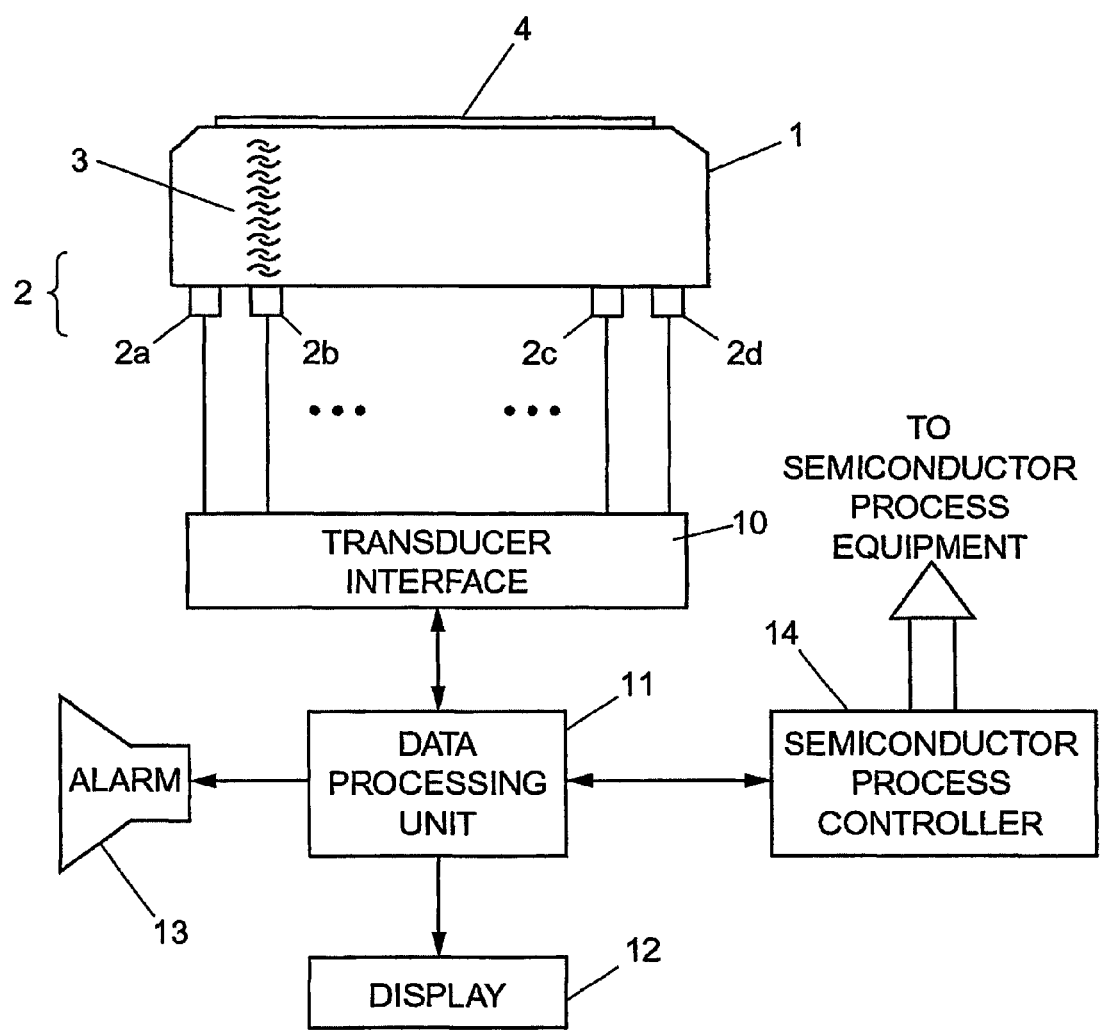
FIG. 1 is a block diagram schematically illustrating an exemplary apparatus for determining the clamping status of a semiconductor wafer 4 on an electrostatic chuck 1.

In describing preferred embodiments of the present invention illustrated in the drawings, specific terminology is employed for the sake of clarity. However, the invention is not intended to be limited to the specific terminology so selected, and it is to be understood that each specific element includes all technical equivalents that operate in a similar manner to accomplish a similar purpose.

The concept of ultrasonics is that if an ultrasonic wave is introduced into an object, it will be partially reflected back from any interface in that object. Therefore, if an ultrasonic transducer is applied to an object and the resultant reflection images are suitably processed, a considerable amount of information about the object can be determined.

In an exemplary embodiment of the instant invention shown in FIG. 1, one or more ultrasonic transducers 2a, 2b, 2c, 2d (collectively referred to herein as element 2) are placed on the backside of a wafer chuck 1. For example, the ultrasonic transducers 2 can be either piezoelectric or electro-mechanical/acoustic transducers (EMAT) and can be attached to the wafer chuck 1 by any suitable means. By observing the reflection patterns of ultrasonic waves (schematically indicated by reference numeral 3), the status of the clamping of a wafer 4 to chuck 1 is determined.

FIG. 1 illustrates a transducer interface unit 10, which allows a data processing unit 11 to control the application of electrical signals to the various transducers 2a, 2b, 2c, 2d and so forth, so that the transducers propagate ultrasonic waves into chuck 1. Transducer interface unit 10 also receives the return signals indicative of the reflected ultrasonic waves, and reports the magnitude of these signals as a function of time to data processing unit 11.

Data processing unit 11 analyzes the return signals to form decisions as to the clamping status of the wafer on the chuck. Any interpretive reports that the data processing unit may generate, as well as the raw return signals, may be presented to users on display 12.

Further, when an alarm condition is present, such as when the wafer process should be stopped due to improper clamping of the wafer or incomplete de-clamping when it is desired to mechanically remove the wafer, then the data processing unit may cause an audible or other type of alarm 13 to be activated. The user may control the semiconductor process accordingly, or, in an alternative embodiment, the data processing unit 11 may control the semiconductor process controller 14 directly.

Transducer interface 10, data processing unit 11, display 12 and alarm 13 may be of conventional design, and are commercially available or readily designed by those skilled in the art. For example, data processing unit 11 may be any suitable general purpose or special purpose computer that is capable of executing programs implementing the methods described later in this specification. Semiconductor process controller 14 is not an element of the present invention as such, but is understood to already be provided as part of the semiconductor process equipment with which the invention may be practiced. Accordingly, additional details of these elements need not be provided herein.

Figure 2A:
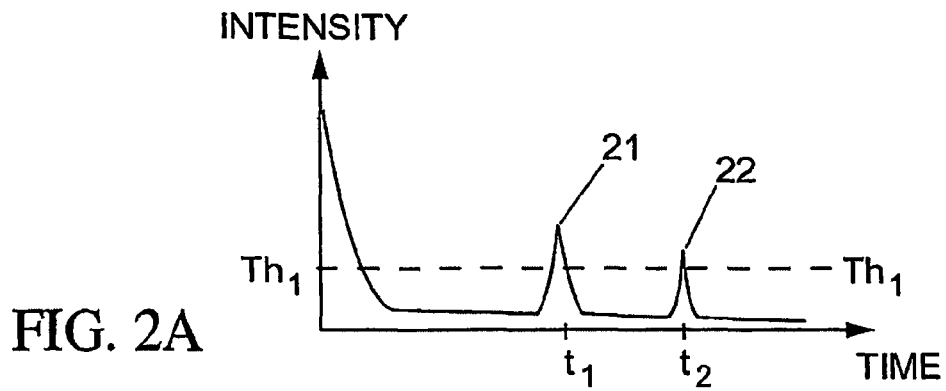
FIGS. 2A, 2B and 2C illustrate ultrasonic intensity as a function of time, for scenarios in which a semiconductor wafer is securely attached to an electrostatic chuck (FIG. 2A), the wafer is partially removed from the chuck (FIG. 2B), and the wafer is completely removed from the chuck (FIG. 2C)

Referring again to FIG. 1, when wafer 4 is intimately clamped to wafer chuck 1, an ultrasonic wave 3 propagates across the interfaces created therein. As shown in the plot of ultrasonic wave intensity as a function of time shown in FIG. 2A, first and second reflections (echoes) 21, 22 are generated. The first and second reflections occur at times $t_1$ and $t_2$, respectively.

First reflection 21 is from the interface between wafer 4 and chuck 1, and second reflection 22 is from the interface on the far side of wafer 4. According to one embodiment of the invention, the relative intensities of the two reflections 21, 22 in FIG. 2A determine that wafer 4 is securely clamped to chuck 1. For example, secure clamping is confirmed by the fact that the intensity of second peak 22 at time $t_2$ is greater than a first intensity threshold $Th_1$.

The invention recognizes that, if plural ultrasonic transducers 2 are employed, the clamping status of wafer 4 as a function of position around chuck 1 may be determined. Accordingly, plural transducers 2a, 2b, 2c, 2d and so forth, are provided, and may function in the same manner as described above for a single transducer, except that the ultrasonic waves are launched in a time-division multiplexed manner so as to avoid confusion of echoes from neighboring transducers.

Figure 2B:
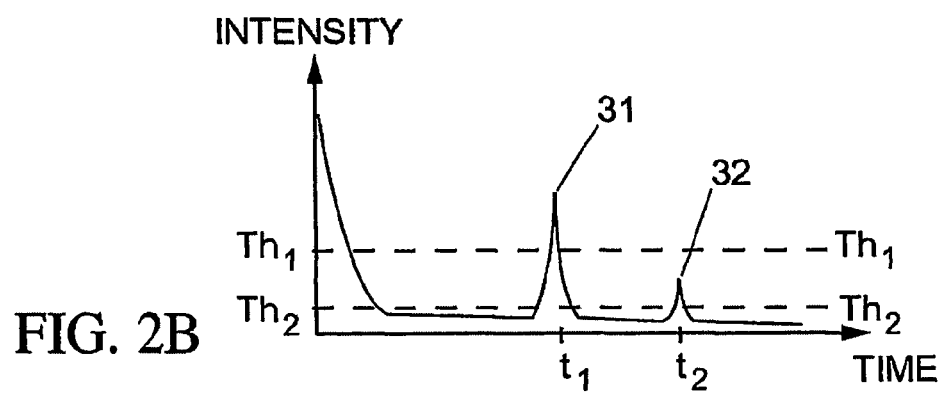

When wafer 4 is to be de-chucked, electrostatic potential is removed. Partial (incomplete) release of the wafer 4 from the wafer chuck 1 is shown from the ultrasonic reflection pattern as shown in FIG. 2B. As wafer 4 is released from chuck 1, there is reduced propagation of the ultrasonic wave 3 across the interface. In that case, there continues to be a single reflection 31 from the top of the chuck 1, but the second reflection 32 from the upper surface of the wafer 4 is of diminishing intensity after the electrostatic potential is removed. This is confirmed when the intensity of second peak 32 at time $t_2$ is less than first intensity threshold $Th_1$ (mentioned above) but greater than a second intensity threshold $Th_2$. Second intensity threshold $Th_2$ is less than first intensity threshold $Th_1$.

Figure 2C:
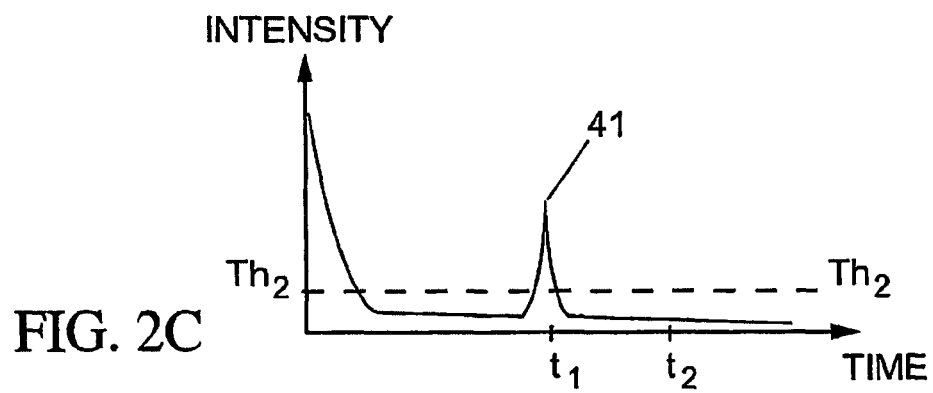

When wafer 4 is completely removed from the surface of chuck 1 (as distinguished from the partial release discussed immediately above), the second reflection from the upper surface of wafer 4 can disappear entirely. For example, the disappearance of the second reflection can confirm that the wafer 4 is no longer present on the surface of chuck 1. This waveform is shown in FIG. 2C, which shows only a first reflection 41. Alternately, there is no second intensity peak at time $t_2$ that exceeds second intensity threshold $Th_2$.

In plural-transducer embodiments such as that illustrated in FIG. 1, plural transducers 2 ensure that wafer 4 is completely released at various locations around the chuck, and that it is safe for the robotic system to remove the wafer.

Threshold values $Th_1$ and $Th_2$ can be determined as absolute numbers, by direct experimentation with a particular setup. Alternatively, to reduce such experimentation, threshold values $Th_1$ and $Th_2$ can be determined as respective fractions of first peak intensity value at time $t_1$.

Figure 2D:
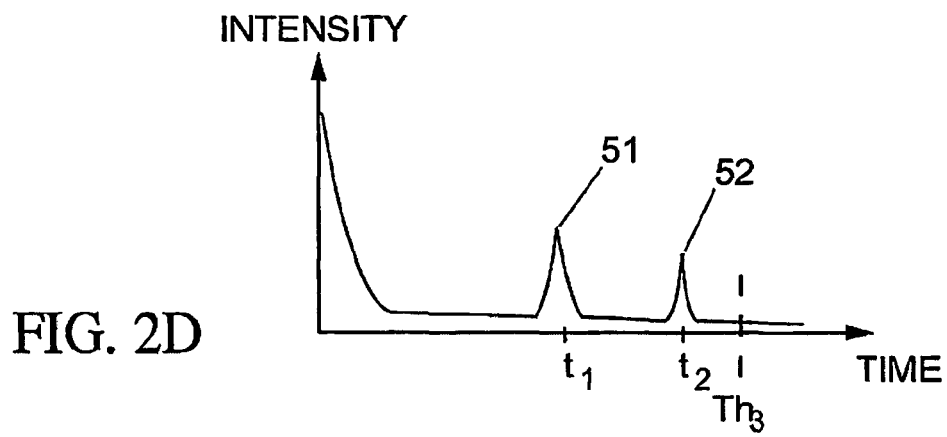
FIGS. 2D, 2E and 2F illustrate another example of ultrasonic intensity as a function of time, for scenarios in which a semiconductor wafer is securely attached to an electrostatic chuck (FIG. 2D), the wafer is partially removed from the chuck (FIG. 2E), and the wafer is completely removed from the chuck (FIG. 2F)
Figure 2E:
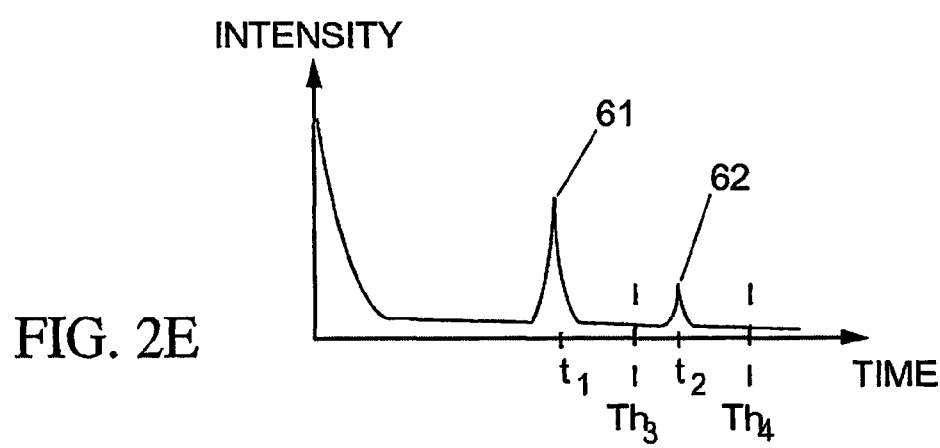
Figure 2F:
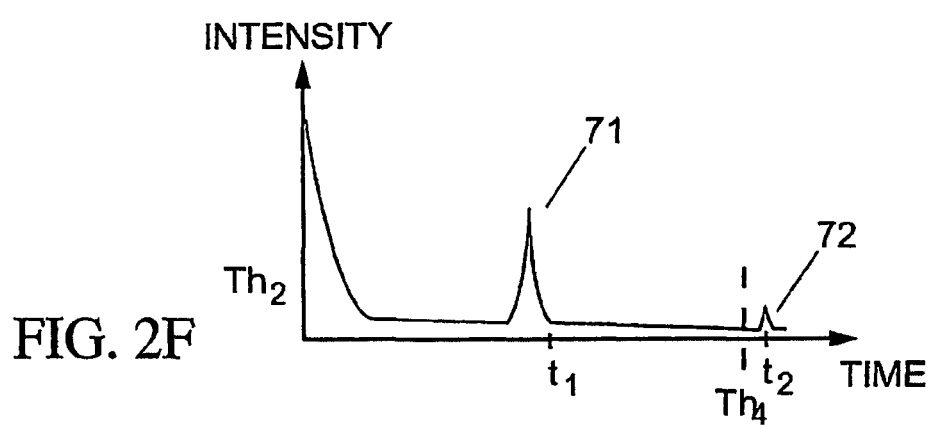

In an alternative embodiment shown in FIGS. 2D–2F, the clamping status can be determined from the time difference between two reflections. For example, the time difference between peak 51 at time $t_1$ and peak 52 at time $t_2$ shown in FIG. 2D can be less than a first threshold difference $Th_3$, indicating secure clamping; the time difference between peak 61 at time $t_1$ and peak 62 at $t_2$ shown in FIG. 2E can be greater than the first threshold difference $Th_3$ and less than a second threshold difference $Th_4$, indicating partial clamping; and the time difference between peak 71 at time $t_1$ and peak 72 at time $t_2$ shown in FIG. 2F can be greater than the second threshold difference $Th_4$, indicating de-clamping.

Time dependent thresholds $Th_3$ and $Th_4$ can be determined as absolute numbers, by direct experimentation with a particular setup. Alternatively, to reduce such experimentation, time dependent thresholds $Th_3$ and $Th_4$ can be determined as respective time delays added to an echo signal occurring at a shorter time These echo signals can originate from reflections from different material layers in chuck 1 or from reflection from the space between chuck 1 and wafer 4 (first intensity peak at $t_1$).

In yet another embodiment, the clamping status can be determined using echo signal (not shown) corresponding to reflection from the lower surface of the wafer 4. This reflection is expected to substantially overlap with first intensity peak at $t_1$ when the wafer 4 is securely clamped to chuck 1. When the wafer 4 is partially or completely released from the surface of chuck 1, the peak corresponding to reflection from the bottom of wafer 4 will occur at a time that is greater than the first intensity peak at time $t_1$.

Figure 3A:
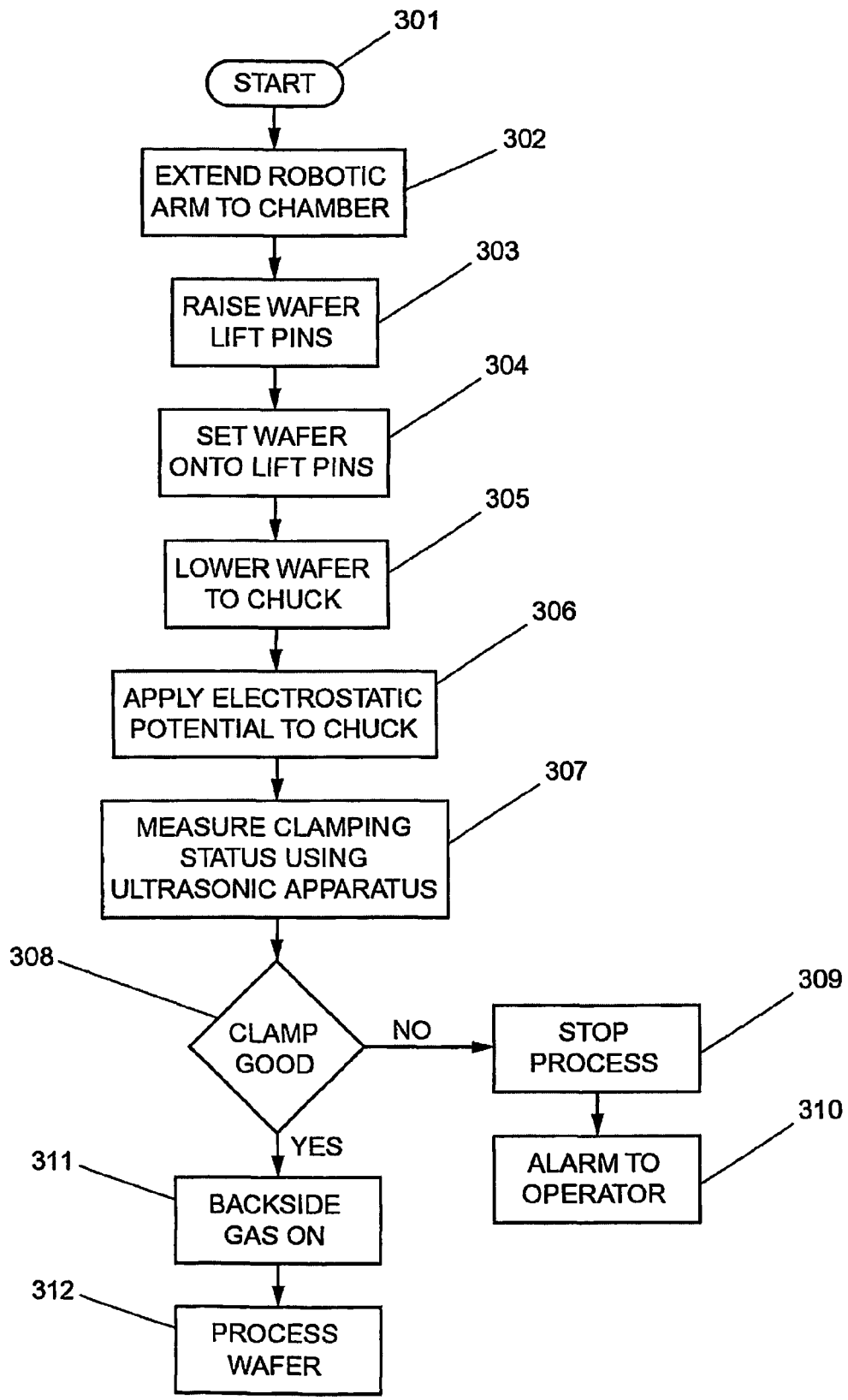
FIGS. 3A and 3B (which may be collectively referred to herein as "FIG. 3") are flow charts illustrating exemplary methods of ensuring that a semiconductor wafer is securely clamped to a chuck before a semiconductor process is started (FIG. 3A), and of ensuring that a semiconductor wafer is properly de-clamped from the chuck before the wafer is mechanically lifted from the chuck after the semiconductor process is completed (FIG. 3B)
Figure 3B:
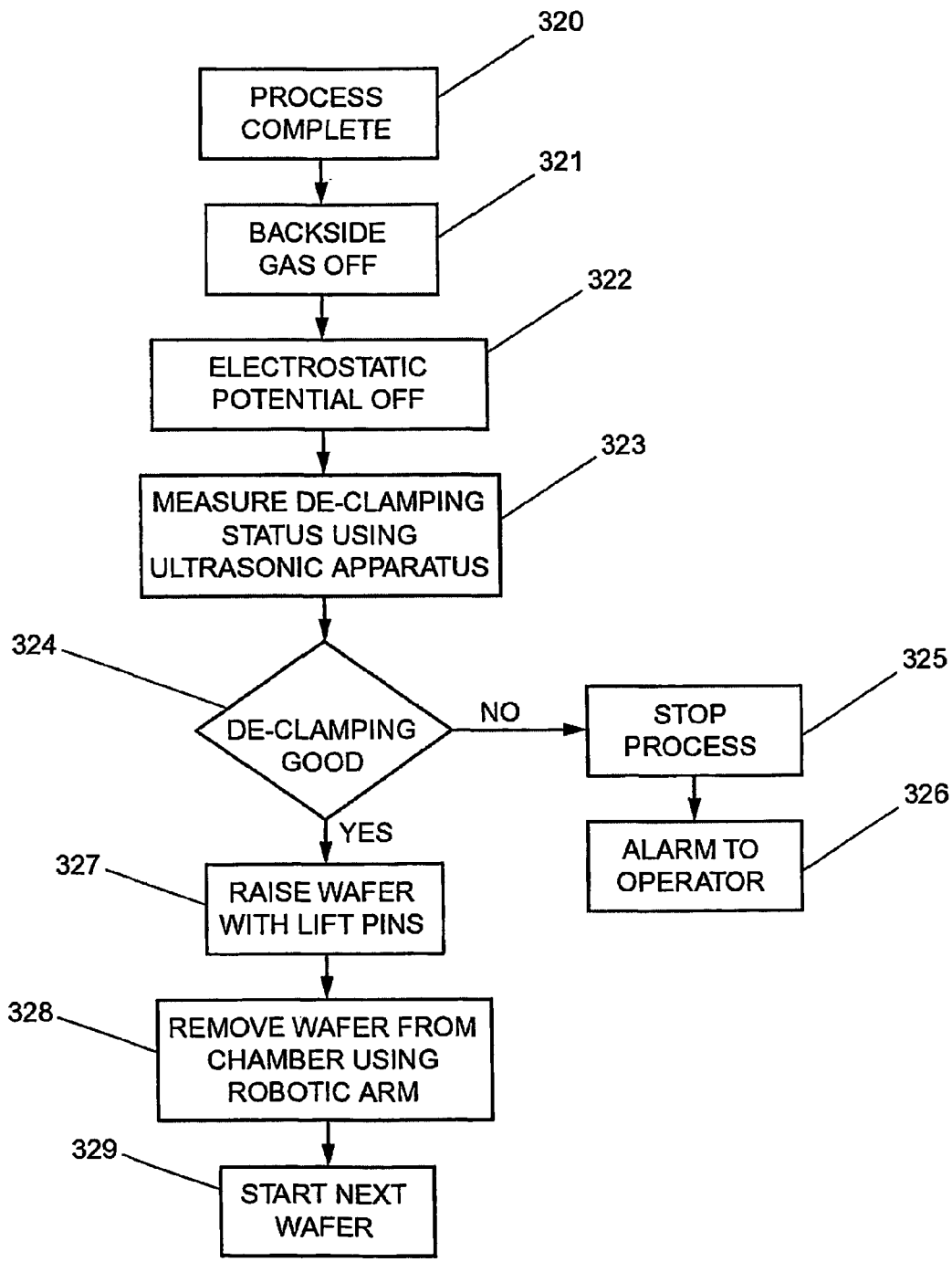

FIGS. 3A and 3B (which may collectively be referred to herein as FIG. 3) show exemplary methods of operation provided by the present invention. FIG. 3A shows an exemplary method by which secure clamping of a wafer to a chuck is verified, before the wafer is processed. FIG. 3B shows an exemplary method for verifying proper de-clamping of the wafer from the chuck before removal of the wafer upon completion of the wafer process.

Referring to FIG. 3A, step 301 starts the method. The robotic arm loads the wafer into the chamber in step 302, and sets the wafer on the lift pins in step 304 that were raised in step 303. The wafer is then lowered to the chuck in step 305, and electrostatic clamping force is applied in step 306.

Step 307 determines the status of the wafer clamping using ultrasonic techniques described above. If the clamp is not good, the sequence proceeds to step 309 in which the process is stopped and proceeds to step 310 in which an alarm is sent to the operator. If the clamp is determined to be good, the sequence proceeds to turn the backside gas on in step 311 and to process the wafer in step 312. Alternately, steps 307-310 can be run after step 311 and also after step 312. FIG. 3B shows an exemplary method for verifying proper de-clamping of a wafer from a chuck before removal of the wafer upon completion of a wafer process.

Referring to FIG. 3B, when the process is complete as determined in step 320, the backside gas is turned off in step 321, and the electrostatic clamping potential is turned off in step 322. Step 324 determines if the wafer has been properly de-clamped in accordance with the principles described above. If the wafer has not been properly de-clamped, the operation is stopped at step 325 and an alarm is sent to the operator in step 326. If the wafer has been successfully de-clamped, it may be safely raised with the lift pins in step 327 and then be removed from the processing chamber by the robotic arm in step 328. At this time, the next wafer sequence may begin (step 301 in FIG. 4A), as shown in step 329.

In an alternate embodiment, a procedure can be performed to ensure that the proper clamping pressure is applied. Clamping the wafer too securely causes excessive numbers of particles to be generated on the back of the wafer. Confirming that the wafer is adequately clamped allows one to limit the clamping force to the amount required to clamp the wafer. In this way, one may avoid using force in excess of the required force to clamp the wafer and thereby, avoid creating troublesome particles. Applying this method in real time may allow one to adjust the clamp force (by increasing the electrostatic voltage) as required to keep the wafer securely in place as the backside gas pressure varies.

Figure 4:
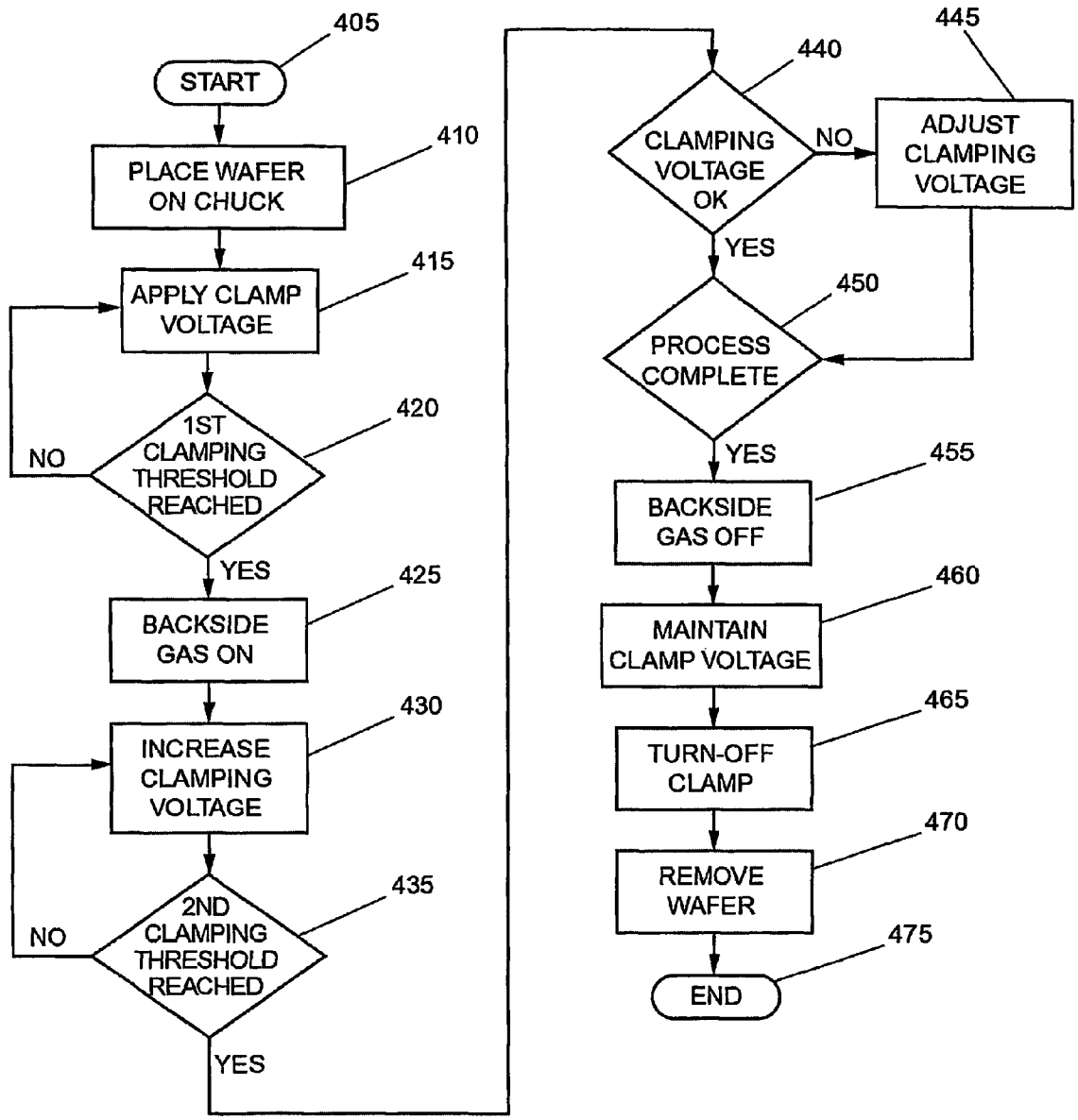
FIG. 4 shows an exemplary method for verifying proper clamping pressure of a wafer on a chuck during a wafer process.

FIG. 4 shows an exemplary method for verifying proper clamping pressure of a wafer on a chuck during a wafer process. Procedure 400 starts in step 405.

In step 410, the wafer is placed on the chuck.

In step 415, voltage is applied to clamp the wafer to the chuck. Clamp voltage can generate force in excess of the force necessary to hold the wafer. Typically equipment is configured for worst case conditions and then every condition is handled as though it is worst case.

In step 420, a query is performed to determine when the clamping voltage reaches a first clamping threshold. A sufficient voltage is applied to clamp the wafer, but only to reach the first "clamping" threshold. When the first clamping threshold is exceeded, procedure 400 continues to step 425. When the first clamping threshold is not exceeded, procedure 400 branches back to step 415.

In step 425, the backside gas is turned on and backside of wafer is pressurized.

In step 430, the clamping voltage is increased.

In step 435, a query is performed to determine when the clamping voltage reaches a second clamping threshold. A sufficient voltage is applied to clamp the wafer, but only to reach the second "clamping" threshold. Desirably, the second clamping threshold is slightly different than the first clamping threshold. When the second clamping threshold is exceeded, procedure 400 continues to step 440. When the second clamping threshold is not exceeded, procedure 400 branches back to step 430.

In step 440, a query is performed to determine if the clamping voltage is correct. The "correct value" is established by providing an operational range around the second clamping threshold voltage. Desirably, the operational range provides for changes in the backside gas. When the clamping voltage is correct, procedure 400 continues to step 450. When the clamping voltage is not correct, procedure 400 branches to step 445 where the clamping voltage is adjusted.

In step 450, a query is performed to determine if the process is completed. Desirably, the clamping voltage is monitored during a process to account for changes in the backside gas pressure. When the process is completed, procedure 400 continues to step 455. When the process is not completed, procedure 400 branches back to step 440.

In step 455, the backside gas is turned-off.

In step 460, the clamping voltage is maintained as the backside gas pressure changes.

In step 465, the clamping voltage is turned off. In step 470, the wafer is removed and procedure 400 ends in step 475.

Modifications and variations of the above-described embodiments of the present invention are possible, as appreciated by those skilled in the art in light of the above teachings. For example, the number and arrangement of transducers on the chuck, and the particular implementations of elements such as the transducers, interface and data processing unit, may be varied while remaining within the scope of the present invention. It is therefore to be understood that, within the scope of the appended claims and their equivalents, the invention may be practiced otherwise than as specifically described.

The invention claimed is:

1. An apparatus for determining how well a semiconductor wafer is clamped to a support member, the apparatus comprising:
   an ultrasonic transducer configured to emit ultrasonic energy toward an interface between the semiconductor wafer and the support member, so that echo signals are generated, the echo signals including a first intensity peak occurring at a first time; and
   a data processing unit configured to analyze the echo signals for a second intensity peak occurring at a second time after the first time to arrive at a determination as to how well the semiconductor wafer is clamped to the support member based on a comparison of at least said second intensity peak to a threshold value.

2. The apparatus of claim 1, wherein:
   the data processing unit is configured to analyze the echo signals to determine that the semiconductor wafer is securely clamped to the support member if the second intensity peak is larger than a first threshold intensity.

3. The apparatus of claim 2, wherein:
   the first threshold intensity is determined as a fraction of the first intensity peak.

4. The apparatus of claim 1, wherein:
   the data processing unit is configured to analyze the echo signals to determine that the semiconductor wafer is completely de-clamped from the support member if the second intensity peak is smaller than a second threshold intensity.

5. The apparatus of claim 4, wherein:
   the second threshold intensity is determined as a fraction of the first intensity peak.

6. The apparatus of claim 1, wherein:
   the data processing unit is configured to analyze the echo signals to determine that semiconductor wafer is neither securely clamped to the support member nor safely de-clamped from the support member if the second intensity peak is between a first threshold intensity and a second threshold intensity.

7. The apparatus of claim 6, wherein:
   the first threshold intensity and the second threshold intensity are determined as respective fractions of the first intensity peak.

8. The apparatus of claim 1, wherein:
   the support member is an electrostatic chuck that clamps the semiconductor wafer by application of electrostatic potential.

9. The apparatus of claim 1, wherein:
   the data processing unit is configured to present a display to a user indicating its determination as to how well the semiconductor wafer is clamped to the support member.

10. The apparatus of claim 1, wherein:
    the data processing unit is configured to send a signal to a semiconductor process controller, indicating the data processing unit's determination as to how well the semiconductor wafer is clamped to the support member.

11. The apparatus of claim 1, further comprising:
    additional ultrasonic transducers configured to emit additional ultrasonic energy toward the interface between the semiconductor wafer and the support member, so that additional echo signals are generated allowing the data processing unit to analyze the additional echo signals from plural additional sites on the support member to arrive at the determination as to how well the semiconductor wafer is clamped to the support member.

12. A method for determining how well a semiconductor wafer is clamped to a support member, the method comprising:
    emitting ultrasonic energy toward an interface between the semiconductor wafer and the support member, so that echo signals are generated, the echo signals including a first intensity peak occurring at a first time; and
    analyzing the echo signals for a second intensity peak occurring at a second time after the first time to determine how well the semiconductor wafer is clamped to the support member based on comparison of at least the second intensity peak to a threshold value.

13. The method of claim 12, wherein:
    the analyzing step includes analyzing the echo signals and determining that the semiconductor wafer is securely clamped to the support member if the second intensity peak is larger than a first threshold intensity.

14. The method of claim 13, wherein:
    the first threshold intensity is determined as a fraction of the first intensity peak.

15. The method of claim 12, wherein:
    the analyzing step includes analyzing the echo signals and determining that the semiconductor wafer is completely de-clamped from the support member if the second intensity peak is smaller than a second threshold intensity.

16. The method of claim 15, wherein:
    the second threshold intensity is determined as a fraction of the first intensity peak.

17. The method of claim 12, wherein:
    the analyzing step includes analyzing the echo signals and determining that the semiconductor wafer is neither securely clamped to the support member nor safely de-clamped from the support member if the second intensity peak is between a first threshold intensity and a second threshold intensity.

18. The method of claim 17, wherein:
    the first threshold intensity and the second threshold intensity are determined as respective fractions of the first intensity peak.

19. The method of claim 12, wherein:
the support member is an electrostatic chuck that clamps the semiconductor wafer by application of electrostatic potential.

20. The method of claim 12, further comprising:
presenting a display to a user indicating the determination as to how well the semiconductor wafer is clamped to the support member.

21. The method of claim 12, further comprising:
sending a signal to a semiconductor process controller, indicating the determination as to how well the semiconductor wafer is clamped to the support member.

22. The method of claim 12, further comprising:
emitting additional ultrasonic energy toward the interface between the semiconductor wafer and the support member, so that additional echo signals are generated allowing the analyzing step to analyze the additional echo signals from plural additional sites on the support member to arrive at the determination as to how well the semiconductor wafer is clamped to the support member.

23. A method of ensuring that a semiconductor wafer is securely clamped to a support member before a semiconductor process is started, the method comprising:
 a) placing the semiconductor wafer in proximity to the support member;
 b) applying a force that tends to clamp the semiconductor wafer to the support member;
 c) measuring a degree by which the semiconductor wafer is clamped to the support member, to arrive at a determination of whether the semiconductor wafer is securely clamped to the support member, wherein the measuring step includes:
  1) emitting ultrasonic energy toward an interface between the semiconductor wafer and the support member, so that echo signals are generated, the echo signals including a first intensity peak occurring at a first time; and
  2) analyzing the echo signals for a second intensity peak occurring at a second time after the first time to determine whether the semiconductor wafer is securely clamped to the support member based on comparison of at least the second intensity peak to a threshold value; and
 d) based on the determination, either continuing with the semiconductor process or aborting the semiconductor process.

24. The method of claim 23, wherein the force applying step includes:
applying electrostatic potential to the support member.

25. The method of claim 23, wherein the aborting step includes:
communicating an alarm to an operator, indicating that the semiconductor wafer is not securely clamped to the support member.

26. The method of claim 23, wherein:
the analyzing step includes analyzing the echo signals and determining that the semiconductor wafer is securely clamped to the support member if the second intensity peak is larger than a threshold intensity.

27. The method of claim 26, wherein:
the threshold intensity is determined as a fraction of the first intensity peak.

28. The method of claim 23, further comprising:
presenting a display to a user indicating the determination as to whether the semiconductor wafer is securely clamped to the support member.

29. The method of claim 23, further comprising:
sending a signal to a semiconductor process controller, indicating the determination as to whether the semiconductor wafer is securely clamped to the support member.

30. The method of claim 23, further comprising:
emitting additional ultrasonic energy toward the interface between the semiconductor wafer and the support member, so that additional echo signals are generated allowing the analyzing step to analyze the additional echo signals from additional sites on the support member to arrive at the determination as to whether the semiconductor wafer is securely clamped to the support member.

31. The method of claim 23, wherein the force applying step includes:
applying electrostatic potential to the support member;
comparing the applied electrostatic potential to a threshold; and
adjusting the applied electrostatic potential if the threshold is not exceeded.

32. A method for verifying proper de-clamping of a semiconductor wafer from a support member before the semiconductor wafer is removed from the support member upon completion of a semiconductor process, the method comprising:
 a) releasing a force that tends to clamp the semiconductor wafer to the support member;
 b) measuring a degree by which the semiconductor wafer is clamped to the support member, to arrive at a determination of whether the semiconductor wafer is properly de-clamped from the support member, wherein the measuring step includes:
  1) emitting ultrasonic energy toward an interface between the semiconductor wafer and the support member, so that the interface generates echo signals, the echo signals including a first intensity peak occurring at a first time; and
  2) analyzing the echo signals for a second intensity peak occurring at a second time after the first time to determine whether the semiconductor wafer is properly de-clamped from the support member based on comparison of at least the second intensity peak to a threshold value; and
 c) if the determination indicates that the semiconductor wafer is properly de-clamped from the support member, physically removing the semiconductor wafer from the support member and continuing the semiconductor process on a subsequent semiconductor wafer.

33. The method of claim 32, wherein the force releasing step includes:
removing electrostatic potential that had been applied to the support member during the semiconductor process.

34. The method of claim 32, wherein the aborting step includes:
communicating an alarm to an operator, indicating that the semiconductor wafer is not properly de-clamped from the support member.

35. The method of claim 32, wherein:
the analyzing step includes analyzing the echo signals and determining that the semiconductor wafer is properly de-clamped from the support member if the second intensity peak is smaller than a threshold intensity.

36. The method of claim 35, wherein:
the threshold intensity is determined as a fraction of the first intensity peak.

37. The method of claim 32, further comprising:

presenting a display to a user indicating the determination as to whether the semiconductor wafer is properly de-clamped to the support member.

38. The method of claim 32, further comprising:

sending a signal to a semiconductor process controller, indicating the determination as to whether the semiconductor wafer is properly de-clamped from the support member.

39. The method of claim 32, further comprising:

emitting additional ultrasonic energy toward the interface between the semiconductor wafer and the support member, so that additional echo signals are generated allowing the analyzing step to analyze the additional echo signals from additional sites on the support member to arrive at the determination as to whether the semiconductor wafer is properly de-clamped from the support member.

* * * * *